US009550706B2

(12) United States Patent
Corma Canós et al.

(10) Patent No.: US 9,550,706 B2
(45) Date of Patent: Jan. 24, 2017

(54) METHOD FOR OLIGOMERISING ALKENES USING THE ITQ-39 ZEOLITE

(71) Applicants: Avelino Corma Canós, València (ES); Cristina Martínez Sánchez, València (ES)

(72) Inventors: Avelino Corma Canós, València (ES); Cristina Martínez Sánchez, València (ES)

(73) Assignee: ExxonMobil Chemical Patents Inc., Baytown, TX (US)

( * ) Notice: Subject to any disclaimer, the term of this patent is extended or adjusted under 35 U.S.C. 154(b) by 193 days.

(21) Appl. No.: 14/599,544

(22) Filed: Jan. 19, 2015

(65) Prior Publication Data
US 2015/0197463 A1    Jul. 16, 2015

Related U.S. Application Data

(63) Continuation of application No. PCT/ES2013/000172, filed on Jul. 12, 2013.

(30) Foreign Application Priority Data

Jul. 19, 2012  (ES) .................................. 201231138

(51) Int. Cl.
C07C 2/12    (2006.01)
C07C 2/06    (2006.01)
(Continued)

(52) U.S. Cl.
CPC ................. C07C 2/12 (2013.01); B01J 29/70 (2013.01); B01J 29/72 (2013.01); B01J 35/002 (2013.01);
(Continued)

(58) Field of Classification Search
CPC ....... C07C 2/12; C07C 2529/70; B01J 35/002; B01J 29/70; B01J 37/28; B01J 29/72; B01J 2229/42; B01J 2229/186; B01J 2229/34; B01J 2229/37; B01J 2229/123; B01J 2229/40; C10L 1/08; C10L 2270/026; C01B 39/026; C01B 39/48; C10G 50/00; Y02P 20/52

See application file for complete search history.

(56) References Cited

U.S. PATENT DOCUMENTS 4,211,640 A    7/1980   Garwood et al.
4,227,992 A    10/1980  Garwood et al.
(Continued)

FOREIGN PATENT DOCUMENTS

EP   0 293 950    12/1988
EP   1 249 486    10/2002
(Continued)

OTHER PUBLICATIONS

M. Moliner et al., "A New Aluminosilicate Molecular Sieve With a System of Pores Between Those of ZSM-5 and Beta Zeolite", Journal American Chemical Society, 2011, vol. 133, pp. 9497-9505.
(Continued)

Primary Examiner — In Suk Bullock
Assistant Examiner — Youngsul Jeong

(57) ABSTRACT

The invention relates to a heterogeneous method for oligomerising alkenes in order to produce hydrocarbons within a diesel fraction in the present of a catalyst based on the ITQ-39 zeolite. The oligomerisation method described in the present invention includes at least: a. feeding a catalyst containing at least the ITQ-39 zeolitic material into the reactor; b. supplying the reactor with a stream that includes at least one olefinic compound; and c. enabling the catalyst
(Continued)

containing at least the ITQ-39 material and the organic compound to remain in contact during the time required for the reaction to take place.

19 Claims, 2 Drawing Sheets

(51) Int. Cl.

| | |
|---|---|
| C07C 2/02 | (2006.01) |
| C10G 50/00 | (2006.01) |
| C01B 39/02 | (2006.01) |
| C01B 39/48 | (2006.01) |
| B01J 37/28 | (2006.01) |
| B01J 29/72 | (2006.01) |
| B01J 29/70 | (2006.01) |
| C10L 1/08 | (2006.01) |
| B01J 35/00 | (2006.01) |

(52) U.S. Cl.
CPC ............ *B01J 37/28* (2013.01); *C01B 39/026* (2013.01); *C01B 39/48* (2013.01); *C10G 50/00* (2013.01); *C10L 1/08* (2013.01); *B01J 2229/123* (2013.01); *B01J 2229/186* (2013.01); *B01J 2229/34* (2013.01); *B01J 2229/37* (2013.01); *B01J 2229/40* (2013.01); *B01J 2229/42* (2013.01); *C07C 2529/70* (2013.01); *C10L 2270/026* (2013.01); *Y02P 20/52* (2015.11)

(56) References Cited

U.S. PATENT DOCUMENTS

| | | | |
|---|---|---|---|
| 5,234,875 A | | 8/1993 | Han et al. |
| 5,284,989 A | | 2/1994 | Apelian et al. |
| 6,143,942 A | | 11/2000 | Verrelst et al. |
| 8,226,925 B2 * | | 7/2012 | Corma Canos .......... B01J 20/18 423/706 |
| 9,302,971 B2 * | | 4/2016 | Cao .......................... C07C 29/19 |
| 2006/0194999 A1 | | 8/2006 | Brown et al. |
| 2010/0145123 A1 | | 6/2010 | Nicholas et al. |
| 2011/0282123 A1 * | | 11/2011 | Corma ..................... B01J 29/70 585/533 |

FOREIGN PATENT DOCUMENTS

| | | |
|---|---|---|
| EP | 2 119 669 | 11/2009 |
| EP | 2 272 939 | 1/2011 |
| EP | 2 386 354 | 11/2011 |
| FR | 2 837 199 | 9/2003 |
| FR | 2 837 213 | 9/2003 |
| FR | 2 887 538 | 12/2006 |
| FR | 2 894 850 | 6/2007 |
| GB | 2 106 131 | 4/1983 |
| GB | 2 106 533 | 4/1983 |
| WO | WO 95/19945 | 7/1995 |
| WO | WO 95/22516 | 8/1995 |
| WO | WO 02/36491 | 5/2002 |
| WO | WO 03/082780 | 10/2003 |
| WO | WO 2007/079038 | 7/2007 |
| WO | 2007/130055 | 11/2007 |
| WO | WO 2008/092984 | 8/2008 |
| WO | 2009/055227 | 4/2009 |

OTHER PUBLICATIONS

T. Willhammar et al., "Structure and Catalytic Properties of the Most Complex Intergrown Zeolite ITQ 39 Determined by Electron Crystallography" Nature Chemistry, 2012, vol. 4, pp. 188-194.
S. Rossini, Catalysis Today 77 (2003) pp. 467-484: The impact of catalytic materials on fuel reformulation.
G. Egloff, Industrial and Engineering Chemistry, 1936, 28 (12), pp. 1461-1467: Polymer Gasoline.
A. de Klerk, Amer. Chem. Soc., Energy Fuels, 2006, 20, pp. 439-445: Distillate Production by Oligomerization of Fischer-Tropsch Olefins over Solid Phosphoric Acid.
A. de Klerk, Amer. Chem. Soc., Energy Fuels, 2006, 20, pp. 1799-1805: Oligomerization of Fischer-Tropsch Olefins to Distillates over Amorphous Silica—Alumina.
J. H. Coetzee, et al.; Applied Catalysis A: General 308 (2006) pp. 204-209: An improved solid phosphoric acid catalyst for alkene oligomerization in a Fischer-Tropsch refinery.
R. Catani, et al.; Catalysis Today 75 (2002) pp. 125-131: Mesoporous catalysts for the synthesis of clean diesel fuels by oligomerisation of olefins.
M. Casagrande, et al.; Catalysis Communications 6 (2005) pp. 568-572: Solid acid catalysts from clays: Oligomerization of 1-pentene on Al-pillared smectites.
A. P. Vogel, et al.; Clay Minerals, Sep. 1990, v. 25, pp. 355-362: Thermogravimetric Analysis of the Iso-Butene Oligomerization Activity of various forms of synthetic Mica-Montmorillonite.
J. C. Q. Fletcher, et al.; Amer. Chem. Soc., Symposium on Alkylation, Aromatization, Oligomerization and Isomerization of Short Chain Hydrocarbons over Heterogeneous Catalysts, New York , ETATS-UNIS (Aug. 8, 1991) 1991, vol. 36, No. 4 (19 ref.), pp. 605-612: Heterogeneous Oligomerization of Propene Over Heteropoly Acids.
C. T. O'Connor, et al.; Applied Catalysis 16 (1985) pp. 193-207: The Oligomerization of C4 Alkenes Over Cationic Exchange Resins.
S. A. Tabak, et al., AIChE Journal, Sep. 1986, vol. 32, No. 9, pp. 1526-1531: Conversion of Propylene and Butylene over ZSM-5 Catalyst.
M. Di Girolamo, et al.; Oil Gas European Magazine Feb. 2005, vol. 121, Issue 6, pp. 70-76: High Quality Fuel Components from C4 Hydrocarbons.

* cited by examiner

METHOD FOR OLIGOMERISING ALKENES USING THE ITQ-39 ZEOLITE

RELATED APPLICATIONS

The present application is a Continuation of co-pending PCT Application No. PCT/ES2013/000172, filed Jul. 12, 2013, which in turn, claims priority from Spanish Application Serial No. P201231138, filed Jul. 19, 2012. Applicants claim the benefit of 35 U.S.C. §120 as to the PCT application and priority under 35 U.S.C. §119 as to said Spanish application, and the entire disclosures of both applications are incorporated herein by reference in their entireties.

FIELD OF THE INVENTION

Heterogenous process of alkene oligomerization.

BACKGROUND

The oligomerization of light olefins, such as propene and butene, represents a major industrial production and sustainable route for the production of liquid synthetic fuels, free of sulfur and aromatics. These processes allow the production of mixtures of olefinic compounds in the range of gasoline or diesel, depending on the selectivity of the catalyst and the operating conditions.

As described in the state of the art, at high temperatures (>300° C.) and low pressures (≤30 bar) the gasoline yield is increased while high pressures and low temperatures favor formation of heavier oligomers in the diesel fraction.

Alkene oligomerization of low molecular weight to products in the diesel range is achieved with the use of acid catalysts, in such a way that the reaction mechanism involves formation of carbenium ions. To obtain high quality diesel product the degree of branching should be restricted and this problem is solved via two possible strategies: by modifying the acid centers (either their strength or the strength of their environment) or by applying the concept of "shape selectivity", using the catalyst with channels of the adequate size to allow the control of the oligomers growth and the branching degree thereof (*Catal. Today* 77 (2003), 467).

In the literature there are many solid acid catalysts for the oligomerization of light olefines to medium distillates reported.

The solid phosphoric acid (SPA) has been described as catalyst for the oligomerization of olefins derived from Fischer-Tropsch, for the production of "polymerization gasoline" and medium distillates in *Ind. Eng. Chem.* 28 (1936) 1461, *Energy Fuels* 20 (2006) 439 and 1799, and *Appl. Catal.* 308 (2006) 204. It has also been described, as a catalyst in oligomerization processes of streams free from olefines, the mesoporous material Si/Al MCM-41 (*Catal. Today* 75 (2002) 125). These materials have been tested with and without small amounts of metal (Ni, Rh or Pt).

Other catalysts studied for oligomerization reactions of olefines to diesel are clays, as described in *Catal. Commun.* 6 (8) (2005) 25 568 and *Clay Minerals* (3) (1990) 355, heteropolyacids and metal salts thereof (*Preprints ACS Div. Petrol. Chem.* 36 (4) 1991) 605) and cation exchange resins described in *Appl. Catal.* 16 (2) (1985) 193.

Medium pore zeolites have proved to be the most suitable ones for high-quality medium distillates in olefin oligomerization processes. Most studies reported in the literature (eg in *AIChE J.* 32 (9) (1986) 1526) are based on the MFI zeolite. Furthermore, in various patents different structures with 10-membered rings are claimed for this process.

U.S. Pat. No. 4,227,992 and U.S. Pat. No. 4,211,640 claim ZSM-11 as catalyst for olefin oligomerization processes and mention other zeolites such as ZSM-12, ZSM-21 and mordenite TEA. GB2106131 and GB2106533 claim the use of ZSM-5 and ZSM-11, in their protonic form, for the oligomerization of light olefins with a selectivity of 25% by weight, to diesel product with a cetane number of 75.

In the 90s, several medium pore zeolites and their use, as catalysts for the oligomerization of light olefins to high quality oligomers and essentially linear ones, which could become lubricating oils of high viscosity index (VI), were patented, diesel with high cetane number and/or chemical intermediates with high added value. Most of these zeolites were treated to increase their selectivity eliminating the surface acidity in such a way that the quality of the product is increased, what is also known as selectivation process. In U.S. Pat. No. 5,234,875 a ZSM-23 zeolite selectivated by coking is described, the performance thereof to slightly branched products is considerably increased when compared with the unmodified catalyst. slightly branched products increases significantly compared to the unmodified catalyst described. In U.S. Pat. No. 5,284,989 three medium pore zeolites, ZSM-22, ZSM-23 and ZSM-35, are described, treated with dicarboxylic acid to deactivate their surface acidity, for the production of hydrocarbons with a low branching degree, in propylene oligomerization processes. These products can be used as alkylating agents for preparing and biodegradable alkylbenzenes and alkylphenylsulfonates.

Several patents (WO95/19945; WO95/22516; U.S. Pat. No. 6,143,942) claim the use of different medium pore zeolites such as ZSM-22, ZSM-57, ZSM-5, alone or in combination, in light olefin oligomerization processes. Thus, they are able to control the degree of oligomerization of olefins, for example to propylene trimer.

In WO93/082780 zeolite ZSM-23 is selectivated with different contents of collidine and is tested in a tubular fixed bed reactor in oligomerization process of butene streams. The reduction in the branching degree as a result of the selectivation is clearly shown and, in addition, it is observed that the reduction in the branching degree and the increase in selectivity to mono-branched isomers are achieved by deactivating the between 25 and 30% of the acid centers.

US2006/0194999 discloses a catalyst for oligomerization processes that comprises a MWW type acidic zeolite as a substitute for solid phosphoric acid, that produces products corresponding to the gasoline fraction products, with high octane number, and other motor fuels such as diesel.

Silicalite containing Al and Ti has also been proposed as a catalyst for oligomerization of light olefins to high quality jet fuel (jet fuel) diesel fractions (31 Gas Oil (2005) 70; EP0293950; EP1249486).

FR2887538A1 describes the use of different zeolites, MEL, ITH, MFI, NES, EUO, ERI, FER, CHA, MFS, MWW, MTT, TON and MOR, which have been previously dealuminated in a first step, followed by a further addition of silicon, and that have been finally transformed to their protonic or acid form.

FR2894850A1 describes the use of MEL, ITH, MFI, NES, EUO, ERI, FER, CHA, MFS, MWW, MTT, TON and MOR zeolites in oligomerization processes for the obtaining of diesel and jet fuel. The zeolites are impregnated with metals of the series VIB and VIII followed by gas phase deposition of amorphous $SiO_2$ with pore size greater than the pore of the zeolites. The catalyst is used in its acid or protonic form.

FR2837199 and FR2837213 disclose the use of zeolites, MEL, MFI, NES, EUO, FER, CHA, MFS, MWW, NU-85, NU-86, NU-88 and IM-5 as catalysts for the oligomerization step in multistage processes of hydrocarbon conversion.

WO2002/36491 discloses the use of UZM-4 zeolite as catalyst in oligomerization processes, but the patent does not include examples of catalytic applications.

WO2007/079038 describes the use of SSZ-74 zeolite catalyst in oligomerization processes, but the document does not include examples of catalytic applications.

The present invention relates to a process of oligomerization of alkenes based on the use of a catalyst containing ITQ-39, described in WO2008/092984, in which the catalyst is not only very active but it increases the selectivity to diesel fraction and is highly stable against deactivation with the reaction time (TOS: Time on Stream) compared with other catalysts reported to date

DESCRIPTION OF THE INVENTION

In a general manner, the present invention describes a process for the production of the hydrocarbon fraction with boiling points within the typical ranges of diesel, that consists of contacting a feed with one or more alkenes, with a catalyst, under certain conditions.

The present invention relates to a process of oligomerization of alkenes for producing hydrocarbons, comprising at least:
a. Introducing a catalyst containing at least the zeolitic material ITQ-39 in the reactor;
b. Feeding the reactor with a stream comprising at least one olefinic compound;
c. Allow the catalyst containing at least the ITQ-39 material and the organic compound to remain in contact the time necessary for the reaction to take place.

Preferably, the hydrocarbons that are obtained can be used as fuels, most preferably they are hydrocarbons which are within the diesel fraction.

In a preferred embodiment, the olefinic compound is preferably selected from ethylene, propene, butenes, pentenes, hexenes or mixtures thereof. Moreover, such olefinic compound may be present in the stream in a preferred concentration of between 10 and 100% by weight.

In a preferred embodiment, the olefin stream is fed to the reactor that can come, at least in part, from a refining process.

According to another preferred embodiment, the product obtained may be a liquid fuel in the diesel range.

The zeolitic material ITQ-39 (P200700334) has the following composition in its calcined state, anhidrous, which is given by the following empirical formula:

$$x(M_{1/n}XO_2):yYO_2:SiO_2$$

wherein M is selected from $H^+$, an inorganic cation of charge+n and mixtures thereof, X is at least one chemical element in +3 oxidation state, Y is at least a second, chemical element other than Si in +4 oxidation state, x has a value between 0 and 0.3, y has a value between 0 and 0.1, and wherein the synthesized material has a diffraction pattern of X-rays with at least the values of angle 2θ (degrees) and relative intensities (I/I0) described in Table I:

TABLE I

| 2θ (degrees) ± 0.5 | Intensity (I/I$_0$) |
| --- | --- |
| 7.8 | S |
| 8.5 | w (h) |
| 15.8 | W |
| 19.3 | W |
| 21.4 | M |
| 22.0 | S |
| 22.8 | Vs |
| 26.2 | W |
| 27.5 | W |
| 32.0 | W |
| 43.5 | W | wherein "vs" refers to a relative intensity of 60-100, "s" refers to a relative intensity of 40-60, "m" refers to a relative intensity of 20-40, "w" to a relative intensity of 0-20, determined as a percentage depending on the most intense peak, and h refers to the diffraction peak appearing as a shoulder.

The zeolitic material ITQ-39, after being calcined to remove the organic matter occluded in the interior, has a pattern of X-ray diffraction with at least the values of angle 2θ (degrees) and relative intensities (I/I0) described in Table II:

TABLE II

| 2θ (degrees) ± 0.5 | Intensity (I/I$_0$) |
| --- | --- |
| 7.8 | Vs |
| 8.6 | w (h) |
| 14.8 | W |
| 15.8 | W |
| 19.4 | W |
| 21.4 | M |
| 22.1 | S |
| 23.0 | Vs |
| 26.3 | M |
| 27.6 | W |
| 32.0 | W |
| 43.9 | W | wherein vs, s, m, w and h have the same meaning described for Table I.

The zeolitic material ITQ-39 can be synthesized starting from a reaction mixture comprising at least a source of $SiO_2$, one or more sources of tetravalent elements Y selected from Ge, Ti, Sn, V and mixtures thereof, one or more sources of trivalent elements X selected from Al, B, Ga, Fe, Cr and mixtures thereof, a source of inorganic cation M with charge n+, a source of an organic dication SDA-1 with a structure described in Scheme 1:

Scheme 1

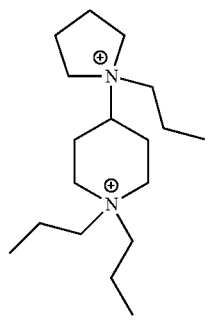

a source of fluoride ions and water, heating the reaction mixture at temperatures between 80 and 200° C. until crystallization is achieved, forming the microporous crystalline zeolitic material ITQ-39, wherein said material has the following composition ranges:

SDA-1(OH)$_2$/SiO$_2$=0.01-1.0,
M$_{1/n}$OH/SiO$_2$=0-0-1,
X$_2$O$_3$/SiO$_2$=0-0.15,
YO$_2$/SiO$_2$=0-0.1
F/SiO$_2$=0.1-3.0, y
H$_2$O/SiO$_2$=0.5-50.

To remove the organic material occluded inside the crystalline microporous structure and thus obtaining the acid form of the zeolite, said synthesized zeolite as described above, can be heated to temperatures above 250° C. for a time between 2 minutes and 25 hours or be subjected to an extraction process or a combination of both treatments.

In a particular embodiment of the present invention, the zeolitic material ITQ-39 can be used in its acid form, where virtually all cation exchange centers are occupied by protons.

In another particular embodiment, the acidity of the zeolitic material ITQ-39 can be partially neutralized. According to this embodiment in which the ITQ-39 can be used in their partially acid form, some of the cation exchange centers of the zeolite are occupied by basic cations rather than protons, preferably selected from metal cations of Group IA and Group IIA protons, (see EP2386354). The amount of cations in ionic exchange centers can be between 1 and 99% (molar), preferably between 2 and 95%, more preferably between 3 and 90% and even more preferably between 10 and 85%, with optimal neutralization levels that depend on the silica/alumina ratio of the starting zeolite and on the basic cation selected. Basic cations can be added during zeolite synthesis or can be added in post-synthesis treatments well-known in the state of the art. Preferably, the cations used are selected from lithium, sodium, potassium, rubidium, cesium and mixtures thereof, preferably sodium, potassium, cesium and mixtures thereof.

According to a particular embodiment of the present invention, the zeolitic material ITQ-39 may also comprise additional cations that may be any stable metal or organic cations, but are preferably selected from V, Cr, Mn, Fe, Co, Ni, Cu, Zn, Mo, W, Y, Ti, Ga, rare earths (e.g. Ce and La), ammonium ions and combinations thereof.

In a further embodiment, if desired, the zeolitic material ITQ-39, either in their acid form or in its partially neutralized form, can be treated with a surface modifying agent (what in the present invention is called selectivation processes), such as a dicarboxylic acid such as oxalic acid, bulky organic molecules (see for example U.S. Pat. No. 4,520,221 and U.S. Pat. No. 4,568,786), collidine or bulky chelating/sequestering agents such as aminocarboxylates (for example ethylenediaminetetraacetic acid (EDTA), diethylenetriaminepentaacetic acid, hydroxyethylethylenediamine triacetate) and aminophosphates or aminophosphonates (eg aminotrimethylenephosphate, tetramethylene ethylenediaminophosphonate) or hexahalosilicate salts. The purpose of this selectivation process through the use of the surface modifying agent is to reduce the content of, or eliminate the content of aluminum outside the zeolite crystals, therefore deactivating the external surface of the zeolitic material. Other selectivation processes considered are selective coking processes or selectivation processes by treatment with sylilating agents well known in the state of the art such as SiCl$_4$ or any hexafluorosilicate salt.

According to another particular embodiment, the ITQ-39 zeolite material can be modified by treating said material with an aqueous solution at pH greater than 8, at a temperature between 25° C. or higher, long enough to generate secondary mesoporosity (WO2011/002630).

According to a particular embodiment, the zeolitic material itq-39 has been modified to generate additional mesoporosity.

In a further embodiment, if desired, the zeolitic material ITQ-39, wherein secondary mesoporosity has been generated by treatment in aqueous solution at a pH>8 and at a temperature between 25° C. or higher, can be selectivated through a surface modifying agent such as for example, dicarboxylic acid, a bulky organic molecule such as collidine, or bulky complexing agents such as EDTA. The outer surface of the ITQ-39 zeolite catalyst with secondary mesoporosity can also be selectively deactivated through selective coking treatments or with silylating agents known in the state of the art as SiCl$_4$ or any hexafluorosilicate salt.

According to a preferred embodiment, the zeolitic material ITQ-39 is deactivated by selectivation processes described above. Preferably, selectivation may be accomplished by treatment with oxalic acid or treatments with ethylenediaminetetraacetic acid (EDTA).

According to a preferred embodiment, the catalyst used based on ITQ-39 zeolite can be formed by at least one matrix comprising, at least, one metal oxide which may be selected from an amorphous oxide, a low crystallinity oxide, or combinations of same. Preferably, the oxide may be selected from alumina, silica-alumina, silica, clays, magnesium oxides, titanium oxide, boron oxide, zirconium oxide, vanadium oxide, chromium oxide, molybdenum oxide, manganese oxide, zinc oxide, iron oxide, nickel oxide, cobalt oxide, tungsten oxide, antimony oxide, cerium oxide, lanthanum oxide and other possible rare earth oxide, preferably selected from alumina, silica-alumina, silica, clays, magnesium oxide, titanium oxide, boron oxide, zirconium oxide and combinations thereof and more preferably is gamma-alumina.

Moreover, the matrix can also comprise, at least, aluminum phosphate, zirconium phosphate, coal, aluminates and combinations thereof.

Preferably the matrix of the catalyst based on zeolite ITQ-39 comprises, at least, one type of silica, alumina, silica-alumina or combinations thereof, preferably gamma-alumina. Binders well known in the state of the art can also be used.

According to a particular embodiment of the present invention, the catalyst based on the ITQ-39 zeolite can further comprise a transition metal, such as V, Cr, Mn hydrogenating metal or any described in the state of the art, for example Group VIII metals or combinations of several of them. The incorporation of these Group VIII metals can be carried out through one or more ion exchange steps or by impregnation techniques or by excess of precursors in the solution, all of them are techniques well known in the state of the art. Sources of Group VIII metal may be, among others, the corresponding nitrates, sulfates, carbonates, halides or combinations of same.

According to a particular embodiment of the present invention the zeolitic catalyst based on ITQ-39 can further comprise at least one Group VIII metal or combinations of more than one of them. Preferably, said metal is selected from iridium, ruthenium, rhodium, rhenium, palladium, platinum, iron, cobalt, nickel and combinations thereof.

According to another particular embodiment of the present invention, the described catalyst may further comprise at least one promoter agent selected from phosphorus, boron and combinations thereof, preferably said promoter agent is phosphorus. These promoters may be included into the catalyst using any technique known in the state of the art. According to this particular case, one could use as a source $H_3PO_4$, $(NH_4)H_2PO_4$, $(NH_4)_2HPO_4$, or combinations thereof.

According to another preferred embodiment, the catalyst may comprise at least one group VIIA element, preferably fluorine.

The catalyst based on zeolite ITQ-39 can be formed in any morphology useful for industrial scale application, such as extrudates, pills, spheres, and microspheres obtained by processes of "spray-dried" among others.

In general, the zeolitic catalyst of the present invention based on the ITQ-39 may have the following composition relative to the total catalyst weight:
   0.1 to 99 wt %, of the zeolitic material ITQ-39;
   0.1 to 99 wt % of matrix;
   0 to 20% of hydrogenating metal typically defined in the state of the art, as for example Group VIII metals.

In a preferred embodiment, the composition percentages are:
   0.5 to 90 wt % of zeolitic material ITQ-39;
   from 0.1 to 75 wt % matrix;
   0 to 10% of the hydrogenating metal.

According to another more preferred embodiment, the composition percentages are:
   1-85 wt % of zeolitic material ITQ-39
   from 0.1 to 60 wt % matrix;
   0 to 5% of hydrogenating metal.

The catalyst based on zeolite ITQ-39 of the present invention may further comprise up to 30%, preferably up to 20% of other promoters, or binding agents among others.

According to a particular embodiment, the feed used in the present invention is composed of at least one olefinic hydrocarbon of between 2 and 10 carbons, and more preferably between 3 and 7 carbons. These olefinic compounds may be selected from ethylene, propene, butenes, pentenes or mixtures thereof. These olefines may be selected from ethylene, propene, butenes, pentenes or mixtures thereof. These olefines may be used pure or mixed with other components such as alkanes (n-propane, n-butane or pentane) or an inert gas like nitrogen. According to a specific embodiment, alkenes should be in a proportion between 10 and 100% by weight of the mixture stream, preferably between 25 and 100%.

The compounds of the feed stream may come from different sources such as oil, natural gas, feeds from biomass and conversion processes as Fischer-Tropsch and other technologies such as gas to liquid (gas to liquid). Moreover, the stream may contain hydrogen, preferably in a molar percentage of between 0.1 and 80% of the stream, more preferably between 0.5 and 50%.

According to a particular embodiment, the olefinic stream may stem, at least in part, from a refining process, such as LPG stream, catalytic cracking product, or the product of a Fischer-Tropsch unit, from biofuel processing units, processing plants of methane to liquid hydrocarbons among others.

The oligomerization process described in the present invention can be carried out in continuous mode, either by contacting the stream with the catalyst in a fixed bed reactor or in a fluidized bed reactor. In the case of fixed bed reactor any known configuration can be used, such as multiple beds operating in parallel in such a way that whereas the reaction takes place in some of them, in other ones the catalyst is being regenerated. In the case of fluidized bed, the reaction can also be configured so that is possible to remove the catalyst from the reaction zone to make it to enter the regeneration cycle.

According to a preferred embodiment, the oligomerization process can be carried out at a temperature between 100 and 500° C., preferably between 120 and 400° C. and more preferably between 150 and 350° C., at a pressure between 0.1 and 200 bar, preferably between 2 and 150 bar and more preferably between 5 and 80 bar, and at a space velocity (WHSV) of the stream on the catalyst from 0.1 to 100 $h^{-1}$, preferably between 0.25 and 50 $h^{-1}$.

The hydrocarbon fraction obtained according to the process of the present invention may comprise more than 10% by weight, preferably more than 35% and most preferably more than 50% by weight of compounds which have a boiling point, under atmospheric conditions, within the typical range of diesel fuel (between 127 and 427° C.), they are preferably compounds between $C_{10}$ and $C_{24}$ (between 174 and 391° C.). Moreover, the hydrocarbon fraction obtained according to the process of the present invention may be subjected to post-treatments such as fractional distillation to recover the pure diesel as well as hydrogenation of the obtained fraction.

In a preferred embodiment, the process of the present invention is carried out in the presence of hydrogen.

The present invention also relates to the use of a catalyst containing at least the zeolitic material ITQ-39 in alkene oligomerization processes for producing hydrocarbons within the diesel fraction.

The examples that follow are intended to illustrate and provide a better understanding of the present invention but are not, in any case, limiting.

EXAMPLES

Example 1

Figure 1:
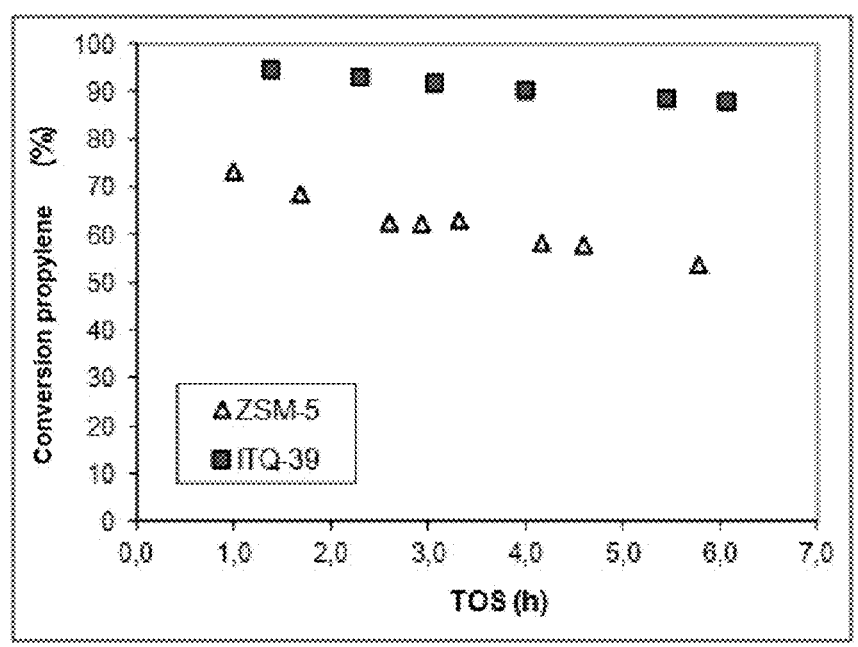
FIG. 1: Conversion of olefin in function of reaction time (Time on Stream, TOS) obtained with zeolite ITQ-39 and ZSM-5 with a commercial origin, in the oligomerization of propylene present in a mixture propylene:propane of 60:40 (molar ratio), at 200° C., 40 bar and a contact time, τ, of 0.08 h.

Preparation of a Dication in a Dihydroxide Form

The organic dication SDA is synthesized following the general process depicted in the following scheme:

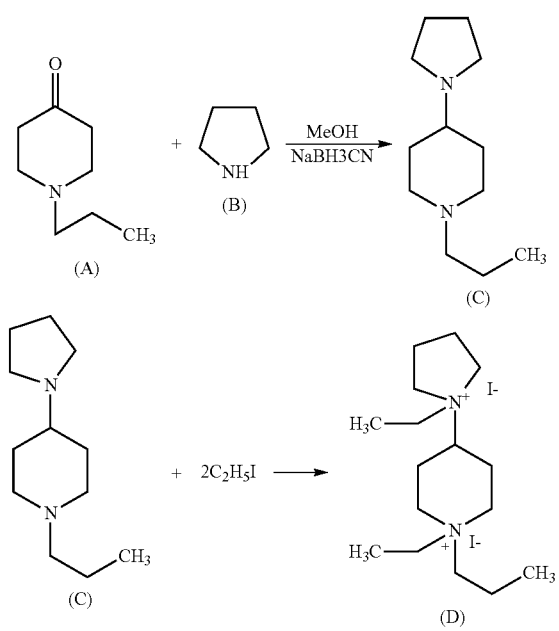

In a general process a reaction of reductive amination of 1-propyl-4-piperidone (compound A) with pyrrolidine (compound B) is performed, leading to the corresponding diamine (compound C). The diamine is quaternized through an ethyl halide being converted into the SDA dication (compound D).

More specifically, the organic dication is prepared as follows:

21.600 g of pyrrolidine are dissolved in 250 ml of methanol and this solution is acidified with HCl (5 M in methanol) to a pH=7.2, cooling the mixture continuously in an external bath at 0° C. Then, 14.30 g of 1-propyl-piperidone, followed by 5.14 g of NaBH$_3$CN are added. The resulting mixture is kept under stirring at room temperature for 72 hours.

HCl (5 M in methane) is slowly added to this mixture, until a pH lower than 2 is achieved by moving the HCN by means of a continuous stream of nitrogen. The resulting solution is concentrated by rotatory evaporation and a solution of KOH (25 wt %) is added until a pH greater than 12 is achieved. At this stage, a white precipitate appears. The resulting mixture was saturated with NaCl and added to water. Finally, the diamine, 1-propyl-4-pyrroline-1-yl-piperidine, is extracted with diethyl ether and dried over anhydrous MgSO$_4$ while stirring.

Quaternization of the diamine is carried out as follows: 65.68 g of ethyl iodide are added to a solution of 19.11 g of diamine in 150 ml of ethanol. 48 hours later, additional 30.80 g of ethyl iodide are added. The mixture is kept stirred at reflux and heated to 85° C. by an external bath. The solution is concentrated by rotatory evaporator.

Several hours later a semi-solid phase is formed. 20 ml of methanol are added to dissolve it and diethyl ether is used for the precipitation of the solid, which is filtered under vacuum.

The iodide of the cation is exchanged with a hydroxide using an ion exchange resin according to the following process: 61.13 mmol of the cationic iodide are dissolved in water. 165 g of Amberlite IRN-78 resin are added to the obtained solution and the mixture is kept under stirring until the next day. The sample is then filtered, washed with ultrapure water and the dihydroxide solution is obtained.

The dihydroxide is titrated with aqueous HCl using phenolphthalein as indicator, obtaining an exchange efficiency greater than 60%. The final solution contains 0.47 equivalents of hydroxide per 1000 g of solution.

Example 2

Synthesis of Zeolitic Material ITQ-39

1883 g of aluminum isopropoxide are added to 28,753 g of tetraethyl orthosilicate (TEOS). Then 146.910 g of the solution obtained in the previous example are added. The mixture is left to evaporate with stirring until complete elimination of the ethanol formed from the hydrolysis of TEOS. At this point 2.92 g of HF (48 wt %) are added. The water is removed by stirring and heating in an external bath to obtain the final composition of the gel, which is:

$SiO_2:0.033Al_2O_3:0.25[SDA](OH)_2:0.5HF:2H_2O$ wherein the SDA is the dication described in Example 1.

The gel is introduced into a stainless steel autoclave with an internal teflon jacket and heated statically for 35 days at 135° C. The solid obtained after separation by filtration, is washed with distilled water and acetone.

The XRD pattern of the synthesized material is shown in Table III

TABLE III

| 2θ (degrees) ± 0.5 | Intensity (I/I$_0$) |
|---|---|
| 7.8198 | 49.56 |
| 8.6885 | 13.82 |
| 15.7045 | 4.51 |
| 19.2097 | 7.54 |
| 21.3591 | 32.59 |
| 22.0000 | 45.40 |
| 22.7964 | 100.00 |
| 25.0561 | 9.92 |
| 26.2576 | 13.17 |
| 27.4230 | 7.01 |
| 28.7596 | 6.87 |
| 29.4369 | 5.87 |
| 31.9616 | 5.07 |
| 34.1133 | 1.72 |
| 36.1252 | 1.17 |
| 36.7736 | 2.03 |
| 42.6035 | 1.28 |
| 43.4655 | 5.76 |

Example 3

Activation by Calcination of the Zeolitic Material ITQ-39

The zeolitic material ITQ-39 obtained as described in example 2 is calcined in an air flow at 580° C. for 3 hours. The DRX pattern of the calcined material is shown in table IV.

TABLE IV

| 2θ (degrees) ± 0.5 | Intensity (I/I$_0$) |
|---|---|
| 7.8461 | 100.00 |
| 8.7039 | 37.71 |
| 11.0092 | 1.47 |
| 13.6688 | 2.40 |
| 14.7903 | 5.20 |
| 15.7731 | 5.95 |
| 19.2573 | 5.47 |

TABLE IV-continued

| 2θ (degrees) ± 0.5 | Intensity (I/I₀) |
|---|---|
| 21.4378 | 28.77 |
| 22.1339 | 44.61 |
| 22.973.9 | 95.99 |
| 25.1759 | 15.59 |
| 26.3257 | 20.77 |
| 27.6284 | 12.92 |
| 29.1717 | 12.52 |
| 32.1493 | 7.69 |
| 34.3923 | 2.64 |
| 36.4259 | 1.95 |
| 43.9105 | 4.31 |

Example 4

Use of Zeolite ITQ-39 as Catalyst for the Oligomerization of Propylene

A zeolitic material ITQ-39 calcined as described in Example 3 is converted into pills, milled and sieved to a particle size of 0.2-0.4 mm. 0.5 g of this sample in the form of pills, are diluted with SiC (0.4-0.6 mm) to obtain a bed volume of 4.0 cm³. The mixture is loaded into a fixed bed reactor of stainless steel, a stream of feed C3=:C3 (60:40 molar ratio) is fed to the reactor in liquid phase through a Gilson piston pump. During the reaction the pressure is controlled by a pneumatic valve electronic Badger. The temperature in the catalytic bed is controlled by two independent heating zones with their corresponding thermocouples placed inside the catalytic bed.

Before starting the oligomerization experiment, the catalyst is activated "in situ" by calcination by increasing the temperature to 520° C. in a flow of 20 ml/min of $N_2$, and calcination for 5 hours at 520° C. in an air flow of 200 ml/min.

Oligomerization experiments are conducted at T=473 K, P=40 bar and a contact time, τ, of 0.08 h, referred to the olefin.

Variation of propylene conversion with reaction time (TOS) obtained with the ITQ-39 zeolitic material, described in this patent is compared in FIG. 1 with the one of a commercial ZSM-5 (Si/Al=11, supplied as ammonium form by TRICAT) tested in the same conditions as the ITQ-39. It can clearly be seen how ITQ-39 is initially more active, and deactivates at lower deactivation speed with TOS than commercial ZSM-5.

Figure 2:
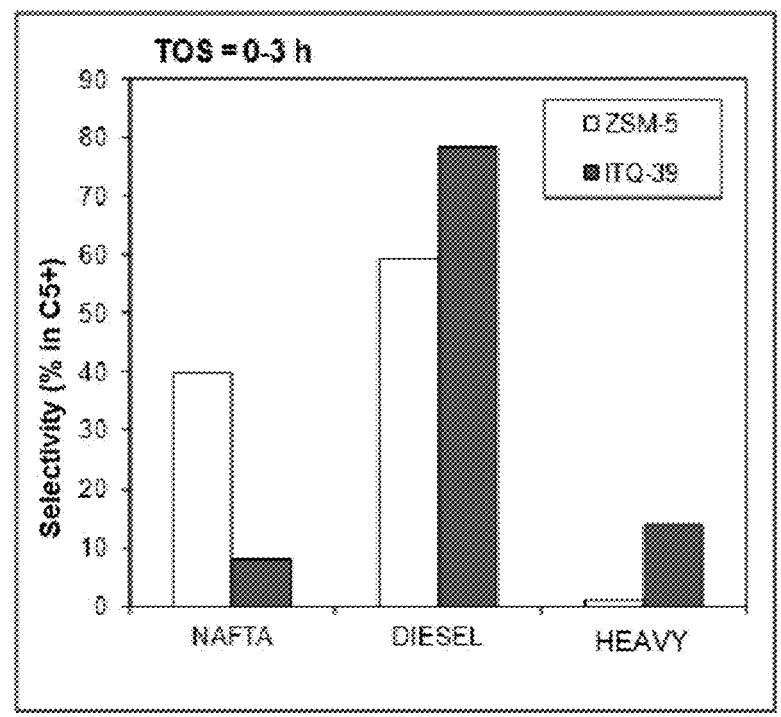
FIG. 2: Selectivity in the C5+ liquid fraction accumulated (TOS=0-3 h and TOS=3-6 h) obtained with the ITQ-39 zeolite and with a ZSM-5 zeolite from commercial sources, in the oligomerization of propylene present in a mixture propylene:propane of 60:40 (molar ratio), at 200° C., 40 bar and at a contact time, τ, of 0.08 h.
Figure 2:
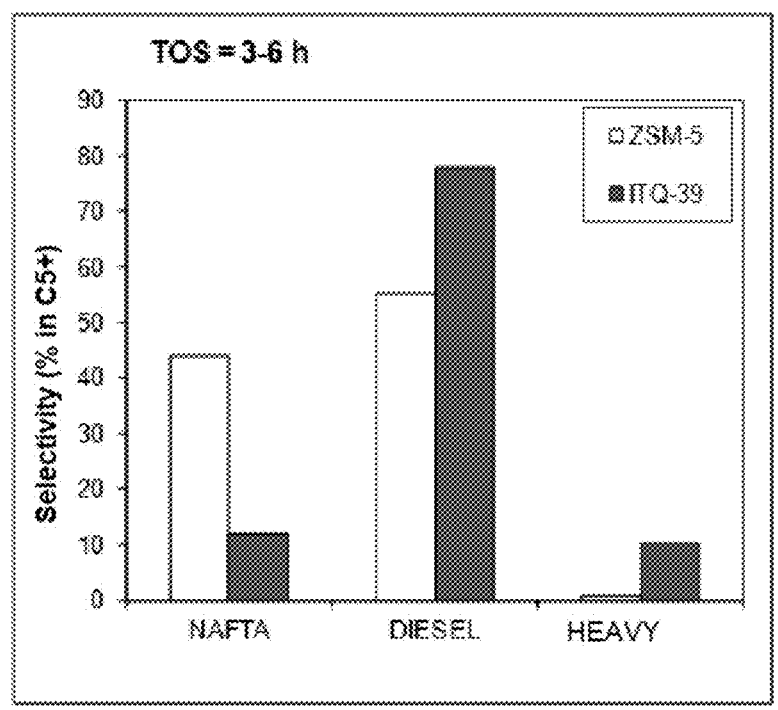

The selectivity to the different fractions in the liquid product, collected at the outlet of the reactor, accumulated at reaction times between 0 and 3 hours and between 3 and 6 hours TOS, is shown in FIG. 2. The results show that the catalyst based on zeolite ITQ-39 is more selective to the desired diesel fraction than the commercial ZSM-5.

The invention claimed is:

1. A process of oligomerization of olefinic compound for producing hydrocarbons, comprising at least:
    a. introducing a catalyst containing at least a zeolitic material ITQ-39 in a reactor;
    b. feeding the reactor with a stream comprising at least one olefinic compound;
    c. allowing the catalyst containing at least the zeolitic material ITQ-39 and the at least one olefinic compound to remain in contact the time necessary for the oligomerization to take place.

2. The process according to claim 1, wherein the olefinic compound is selected from the group consisting of ethylene, propene, butenes, pentenes, hexenes or mixtures of same.

3. The process according to claim 1, wherein the olefinic compound is present in the stream at a concentration between 10 and 100% by weight.

4. The process according to claim 1, wherein the zeolitic material ITQ-39 is in its acid form.

5. The process according to claim 1, wherein the zeolitic material ITQ-39 has been modified to generate additional mesoporosity.

6. The process according to claim 1, wherein the zeolitic material ITQ-39 has a external surface that has been deactivated through selectivation processes.

7. The process according to claim 1, wherein the zeolitic material ITQ-39 has been selectivated through treatments with oxalic acid.

8. The process according to claim 1, wherein the zeolitic material ITQ-39 has been selectivated through treatments with ethylenediaminetetraacetic acid (EDTA).

9. The process according to claim 1, wherein the catalyst comprises a matrix formed by, at least, one oxide selected from the group consisting of amorphous oxide, low crystallinity oxide and combinations thereof.

10. The process according to claim 1, wherein the catalyst comprises a matrix formed by, at least, one oxide selected from the group consisting of alumina, silica-alumina, silica, clays, magnesium oxide, titanium oxide, boron oxide, zirconium oxide, and combinations thereof.

11. The process according to claim 1, wherein the catalyst comprises a matrix formed by gamma-alumina.

12. The process according to claim 1, wherein the catalyst comprises a matrix that comprises at least aluminum phosphates, zirconium phosphates, coal, aluminates and combinations thereof.

13. The process according to claim 1 wherein the catalyst comprises at least one hydrogenating Group VIII metal and combinations thereof.

14. The process according to claim 1, wherein the catalyst comprises at least one metal selected from the group consisting of iridium, ruthenium, rhodium, rhenium, palladium, platinum, iron, cobalt, nickel and combinations thereof.

15. The process according to claim 1 wherein the catalyst comprises at least, a promoter agent selected from phosphorus, boron and combinations thereof.

16. The process according to claim 1 wherein the catalyst comprises at least, a promoter that is phophorus.

17. The process according to claim 1, wherein the catalyst comprises at least, an element of Group VIIB.

18. The process according to claim 1 that it is carried out at a temperature between 100 and 500° C., at a pressure between 0, 1 and 200 bar and at a spatial rate (WHSV) between 0.1-100 h⁻¹.

19. The process according to claim 1, that it is carried out in the presence of hydrogen.

* * * * *